United States Patent [19]
Levesque

[11] 4,016,875
[45] Apr. 12, 1977

[54] PENIS LOCKING AND LACERATING VAGINAL INSERT

[75] Inventor: Alston L. Levesque, Burlingame, Calif.

[73] Assignee: Raymond Lee Organization, Inc., New York, N.Y.

[22] Filed: Apr. 8, 1976

[21] Appl. No.: 675,114

[52] U.S. Cl. .............................. 128/132 R; 2/2.5; 119/143

[51] Int. Cl.² .......................................... A61F 13/00

[58] Field of Search .......... 128/132 R, 127, 138 R, 128/294, 1 R; 119/143; 2/2.5

[56] References Cited

UNITED STATES PATENTS

| 14,993 | 6/1856 | Alley | 128/127 |
|---|---|---|---|
| 28,480 | 5/1860 | Heard | 128/127 |
| 33,162 | 8/1861 | Reynolds | 128/138 R |
| 64,211 | 4/1867 | Ewing | 128/127 |
| 222,368 | 12/1879 | Speer | 119/143 |
| 807,160 | 12/1905 | Foote | 128/138 R |
| 934,240 | 9/1909 | Tunnessen | 128/138 R |
| 3,107,653 | 10/1963 | Goddard | 119/143 |
| 3,854,476 | 12/1974 | Dickinson et al. | 128/138 R |
| 3,913,574 | 10/1975 | Schacht | 128/138 R |

OTHER PUBLICATIONS

E. J. Dingwall, The Girdle of Chastity, A Medico-Historical Study–London–Geo. Routledge & Sons, Ltd.

Primary Examiner—Lawrence W. Trapp
Attorney, Agent, or Firm—Stephen Wyden

[57] ABSTRACT

A plurality of rigid members forming lateral enlargements engage a plurality of housing members having lateral slots to secure the enlargements, springs within the housing press the rigid members distal to the housing to retain the device within a woman's vagina and a blade, which may have barbs on its edge, is pivotally mounted within a slot in the internal surface of the housing.

2 Claims, 5 Drawing Figures

PENIS LOCKING AND LACERATING VAGINAL INSERT

This invention relates to inserts for use within the vagina of a woman for the harming of a man who may insert a penis into the vagina of the woman. This invention represents improvements in such inserts and it provides more efficient means to lock on the penis and to lacerate the locked on penis.

The invention can be understood in view of the accompanying figures.

Figure 1:
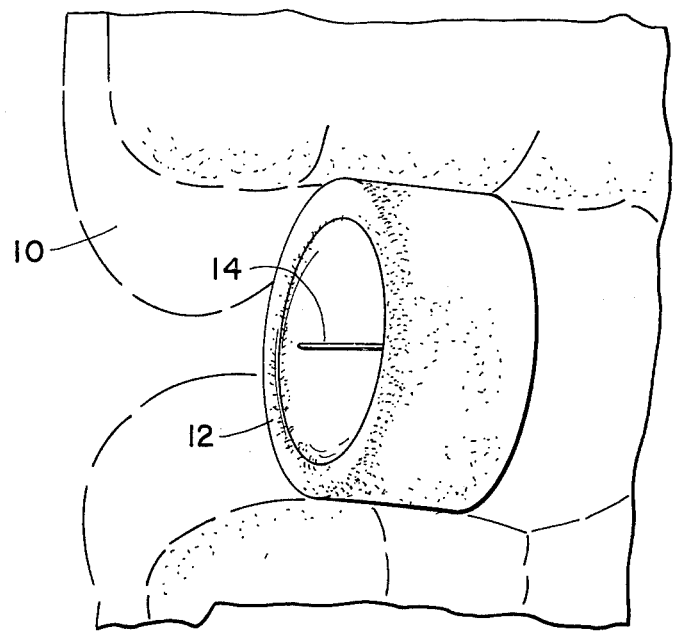
FIG. 1 shows the device inserted within the vagina of a woman.

With regard to FIG. 1, a woman may insert within her vagina 10 the device 12 so that the blades 14 may cut a penis inserted in the vagina or the penis while attempting to be removed from the vagina.

Figure 2:
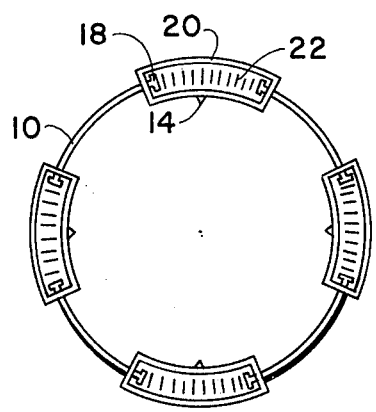
FIG. 2 is an edge on view of the device.
Figure 3:
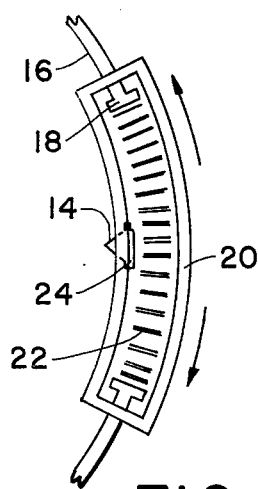
FIG. 3 is a close up of part of the device of FIG. 2.

With regard to FIGS. 2 and 3, the device is seen to consist of a set of rigid members 16 forming enlargements 18 at each of the lateral extremities which retain the rigid members 16 within the curved housings 20. The central aperture formed by the device is kept enlarged by the presence of the steel springs 22 within the housing 20 pressing against the enlargements 18. A slot in the internal face of the housing 20 permits the blade 14 to extend within the central cavity and to pivot 24 into greater proximity to the flesh of the penis as the penis may move forward and back within the locking grip of the device.

Figure 4:
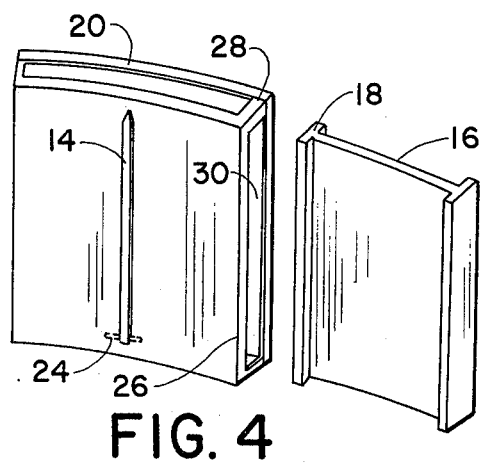
FIG. 4 is a perspective view of several of the components of the device disassembled.

With regard to FIG. 4, the blade 14 is seen to pivot on the pivot pin 24 which is mounted within the housing 20. The housing 20 may be sealed 28 to form a set of side slots 30 after the enlargements 18 of the rigid members 16 has been inserted within the housing. The sealing of the housing 28 retains the rigid member 16 within the confines of the housing 20 and thereby allows for contraction and expansion of the device without the device coming apart.

Figure 5:
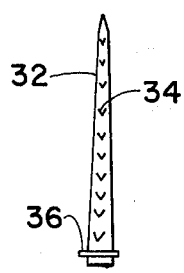
FIG. 5 is a close up of a modified version of the blade.

With regard to FIG. 5, an alternative embodiment of the blade consists of the pivot shaft 36 on which a blade 32 is mounted the edge of which consists of a plurality of barbs 34, whereby the penis may be more thoroughly lacerated.

This device may find use for those women who have enormous fears of being raped. They may also be of value for those women who have extreme discomfort in the presence of a man even on such intimate terms as dating. With this device in her possession a woman may feel secure that if employed a male becoming intimate with her shall not receive pleasure from the experience. The penis may enter this device without great resistance and will activate the blade only upon the attempt of the man to withdraw the penis from the device.

Having described a preferred embodiment of my invention, it is understood that various changes can be made without departing from the spirit of my invention, and, I desire to cover by the appended claims all such modifications as fall within the true spirit and scope of my invention.

What I claim and seek to secure by Letters Patent is:

1. A penis locking and lacerating device, comprising:
   a plurality of rigid members,
   each of the rigid members forming a lateral enlargement of each side of the rigid member,
   a plurality of housing members,
   each of the housing members forming a slot at each side of the housing member within which one of the enlargements of the rigid members may be received,
   means of sealing the housing member slot after insertion of the rigid member enlargement, whereby the rigid member is permanently locked within the housing member,
   spring means of yieldably pressing the rigid members distal to the housing member,
   a slot formed in an internal surface of the rigid housing,
   a blade mounted within the slot in the internal surface of the rigid housing, and
   means of pivoting the blade attached to the blade and mounted within the internal surface of the housing member.

2. The vaginal insert of claim 1, further comprising:
   a plurality of barbs formed on a front edge of the blade, whereby the blade may further lacerate a penis locked within the device.

* * * * *